United States Patent [19]

Desportes et al.

[11] Patent Number: 4,608,155
[45] Date of Patent: Aug. 26, 1986

[54] MAGNETIC SEPARATOR

[75] Inventors: Henri Desportes, Gif sur Yvette; Joao Meyer, Paris, both of France

[73] Assignee: Commissariat a l'Energie Atomique, Paris, France

[21] Appl. No.: 634,570

[22] Filed: Jul. 26, 1984

[30] Foreign Application Priority Data

Aug. 3, 1983 [FR] France .................. 83 12797

[51] Int. Cl.⁴ ............................................. B03C 1/26
[52] U.S. Cl. ................................... 209/224; 209/232; 210/222
[58] Field of Search ............... 209/214, 232, 213, 212, 209/223 R, 224; 210/223, 222

[56] References Cited

U.S. PATENT DOCUMENTS

| 731,038 | 6/1903 | Gates | 209/212 |
| 3,608,718 | 9/1971 | Aubrey et al. | 209/223 |
| 4,239,619 | 12/1980 | Aplan et al. | 209/214 |

FOREIGN PATENT DOCUMENTS 2253567  7/1975  France.
1309089  3/1973  United Kingdom.

Primary Examiner—S. Leon Bashore
Assistant Examiner—Thomas M. Lithgow
Attorney, Agent, or Firm—Kerkam, Stowell, Kondracki, & Clarke

[57] ABSTRACT

Magnetic separator in which the particles forming the mixture to be separated drop from an opening into a separating space, where they are exposed to the action of a magnetic field having a gradient in the horizontal plane and produced outside the separating space.

The magnetic field is of the multipole type having a high dipole component in a direction in a horizontal plane in the separating space, in order to apply a high magnetic force to the magnetized particle, in order to increase the separation as a function of their magnetic susceptibility. The magnetic separator according to the invention can more particularly be used for the separation or cleaning of particles having different magnetic properties.

5 Claims, 4 Drawing Figures

MAGNETIC SEPARATOR

BACKGROUND OF THE INVENTION

The present invention relates to a magnetic separator, which can more particularly used for the separation or cleaning of particles having different magnetic properties.

Such a magnetic separating, sorting or classifying device is constituted by a treatment space immersed in a magnetic field, whose characteristics make it possible to selectively act on substances having different magnetic susceptibilities. The particles treated are subject to different forces, namely a magnetic force linked with the magnetic properties of the substance and forces which are independent of the magnetic properties of the substance, mainly gravitational forces, together with the resistance forces due to viscosity.

It is known that the deflecting effect on a magnetic field of particles having magnetic properties is proportional to the product of this magnetic field by its gradient.

French Pat. No. 2 253 567 describes a magnetic separation process for weakly magnetized particles. This process essentially consists of using a multipole field in the separation space on which is superimposed a substantially homogeneous magnetic field (p. 3, line 5 ff.). More specifically, in the example described (p. 5, line 29 ff.) the divided magnetic field is a quadripole field, on which is superimposed a homogeneous magnetic field produced by a solenoid in the longitudinal direction of the quadripole. The additional feature of the solenoid is in this case perpendicular to the field of the quadripole. Theory, calculation and experience show that in this case the accelerations in the three directions of the space are unchanged, i.e. the gain on the separating power is zero.

In the publication by E. C. Hise, A. S. Holman and F. J. Friedlaender: "Development of high-gradient and open-gradient magnet separation of dry fine coal" in IEEE TRANSACTIONS ON MAGNETICS, vol. 17, no. 6, November 1981, pp. 3314–3316, magnetic separation based on the following method is described.

Particles to be separated fall freely into a volume where an adequate magnetic field is applied. The magnetic field is chosen in such a way that at the end of the fall, the particles having different magnetic susceptibility are collected at different points.

The magnetic separator according to the aforementioned article comprises a stack of coils having a symmetry of revolution. In this configuration, the horizontal component of the separating force is cancelled out on the central axis of this separation space and which is surrounded by coils. When the particle beam to be separated falls in the vicinity of said central axis, the separation in this substantially zero field is mediocre.

SUMMARY OF THE INVENTION

The object of the invention is to obviate this disadvantage and more particularly consists of proposing a magnetic separator incorporating a magnetic configuration ensuring a high magnetic force at the location of the beam of particles to be separated.

The invention specifically relates to a magnetic separator in which the particles constituting the mixture to be separated drops from an inlet port into a separation space, where they are subject to a magnetic field having a gradient in the horizontal plane and produced at the end of the separation space, wherein the magnetic field is of the multipole type, incorporating a high dipole component in a direction in the horizontal plane in the separating space, in order to apply a high magnetic force to the magnetized particles, in order to increase separation as a function of their magnetic susceptibility.

According to a preferred embodiment, of a magnetic separator according to the invention, the magnetic field essentially has a quadrupole configuration superimposed with a dipole configuration in the horizontal plane. Preferably, the dipole configuration is oriented in accordance with the axis passing through two poles of the same polarity of the quadrupole configuration.

According to another feature, the magnetic field is produced by a quadrupole winding surrounded by a dipole winding.

According to another feature, the magnetic fields are produced by superconductor windings.

The invention also relates to a device for measuring the magnetic susceptibility of solid substances, wherein it conforms with the aforementioned magnetic separator.

According to another feature of the magnetic separator according to the invention, the separation space for the magnetized particles is a dry route separator.

According to another feature of the magnetic separator according to the invention, the separating space for the magnetized particles is a wet route separator.

BRIEF DESCRIPTION OF THE DRAWINGS

The invention is described in greater detail hereinafter relative to non-limitative embodiment and with respect to the attached drawings, wherein show.

DETAILED DESCRIPTION OF THE PREFERRED EMBODIMENTS

Figure 1:
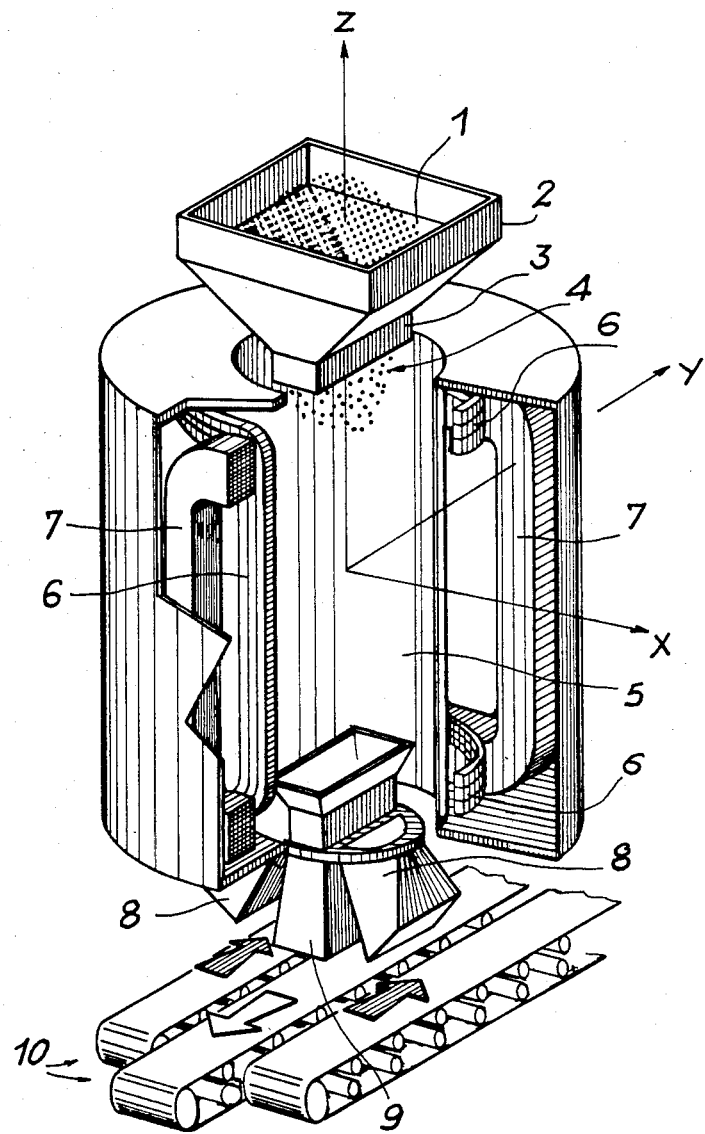
FIG. 1 diagrammatically, an exploded view of a preferred embodiment of a magnetic separator according to the invention.

FIG. 1 shows a magnetic separator.

The granular substance 1 to be separated is located in a container 2 with an opening 3 through which a material particle beam 4 falls freely into a magnetic separating space 5. The latter has a cylindrical volume with a revolution symmetry axis identical to the revolution symmetry axis of the particle beam 4. The space 5 is surrounded by a coil 6 producing a quadrupole magnetic field in the horizontal plane.

By means of a pair of supplementary coils 7, a substantially uniform high dipole field is superimposed on the quadrupole field. The axis of this supplementary field is parallel to the longitudinal axis of the opening 3. This axis is designated y in FIG. 1.

The magnetic particles which drop from the opening are horizontally displaced during their fall, due to the magnetic field gradient. Due to the superimposed dipole field, the magnetization of the substances and consequently the magnetic force on the magnetized particles are much higher than in the case where separation is only performed by means of a quadrupole field.

Figure 3:
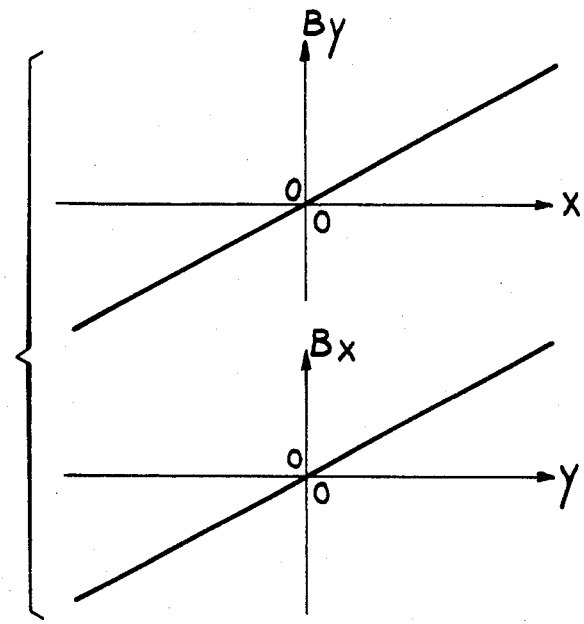
FIGS. 3 and 4 horizontal components of the magnetic induction in arbitrary units, respectively in the case of a pure quadrupole field (FIG. 3) and in the case of superimposing an additional horizontal dipole field (in the x,y plane).
Figure 4:
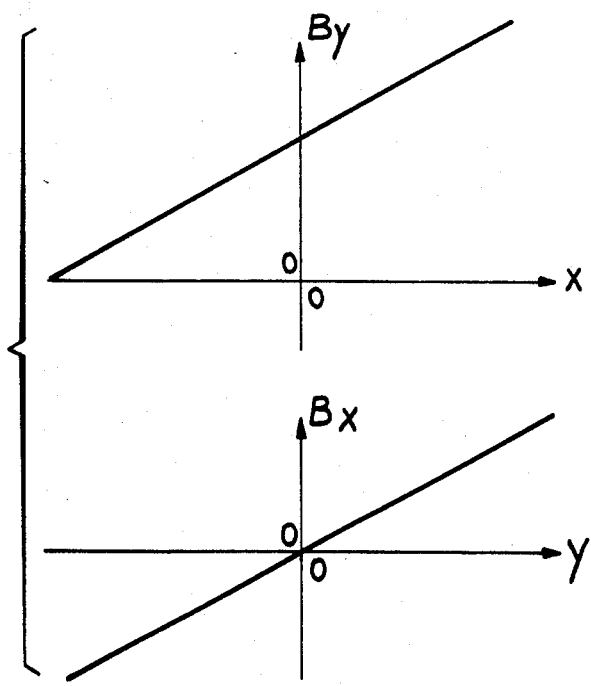

FIGS. 3 and 4 give the horizontal components of the magnetic induction in arbitrary units.

FIG. 3 shows the pure quadrupole case and FIG. 4 the effect of superimposition.

The effect of the supplementary field is made apparent by comparing By in both Figs.

In French Pat. No. 2 253 567, the additional field Bo is parallel to the vertical Oz. We have seen that this constant field has no influence on the horizontal deflection of the magnetic substances and this is why, in the invention, the vertical field is zero.

The supplementary field reinforcing the magnetization of the substance to be separated leads to a gain of an order of magnitude on the separating effect of the gradient resulting from the quadrupole field.

The particles separated in accordance with their magnetic susceptibility are extracted through slots 8, 9.

The magnetic materials drop into slots 8 and the unmagnetized particles drop into the central slot 9. Finally, the separated materials are transported, e.g. using conveyor belts 10 into adequate containers.

In an embodiment of the magnetic separation described hereinbefore, a quadrupole magnetic configuration is used, but it is obvious that it is possible to use a magnetic field having a different configuration. The essence is that the magnetic field supplies a high gradient in a large part of the horizontal plane of the separating space. The exact choice of the configuration is dictated by technical and economic considerations.

Figure 2:
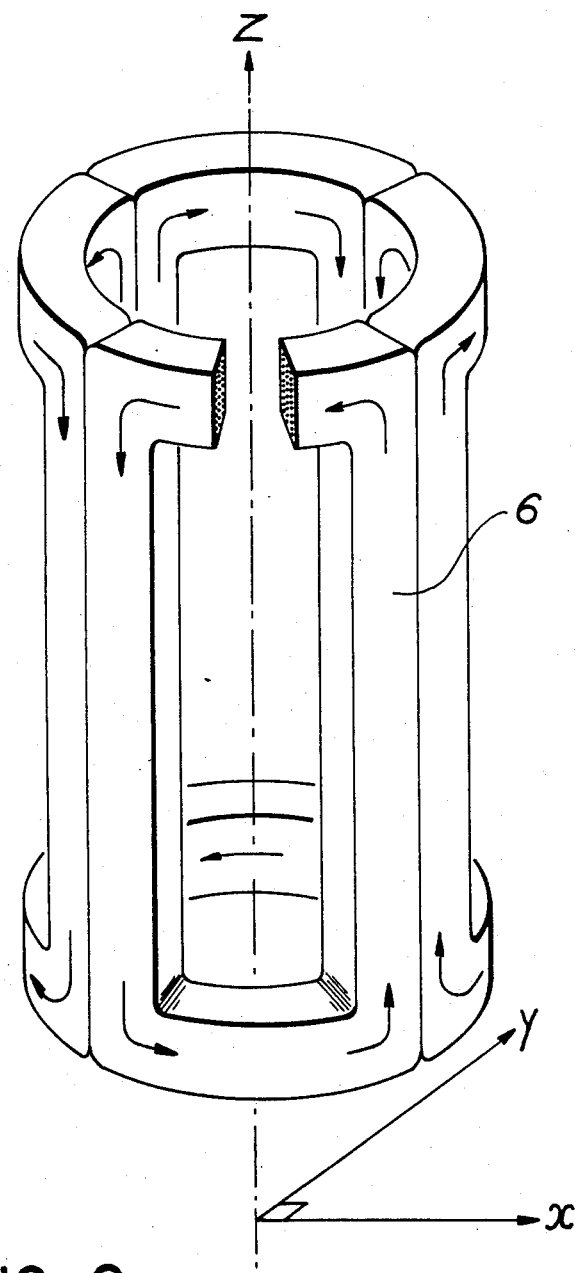
FIG. 2 is a diagrammatic perspective view of the configuration of the coils supplying the quadrupole magnetic field.

FIG. 2 diagrammatically shows a configuration of coil 6 supplying the quadrupole magnetic field. These four coils form a cylinder of central axis Z.

In certain circumstances, superconductor coils have a considerable advantage, particularly when the volume occupied by the separator is considerable, even if the actual fields are not too high ($B<2T$).

High gradients and fields are indispensable in the case of separations of paramagnetic substances. These values can only be obtained by using superconductors.

However, it should be noted that the separation method described hereinbefore is not dependent on superconductors and could, in principle, use resistive coils.

Impacts between magnetized particles and inert particles lead to an inhibition of separation.

The increased horizontal deflection of the magnetized particles provides the advantage that the probability of collisions between magnetized particles and inert particles is greatly increased.

In order to prevent an excessive dispersion of the "images" of the paths of the particles to be separated, in the horizontal plane, it is desirable that the substances to be treated have an adequate magnetic homogeneity.

Hitherto, a description has been given of magnetic separations in which separation takes place by the dry route. It is also possible to use a separator having a magnetic configuration like that described hereinbefore, for separating magnetic materials using the wet route, provided that possible account is taken of the flow rates of the liquids.

Finally, the previously described magnetic sorter can be used as an instrument for measuring the magnetic susceptibility of solid substances. The accuracy can be very good and is only dependent on the accuracy of the knowledge of the gradient of the magnetic field applied to the separating space and the value of the magnetic induction produced by the dipole field.

What is claimed is:

1. A magnetic separator for separating magnetic particles from non-magnetic particles comprising a vertically oriented separation chamber; an inlet for particles to be separated at the top of the chamber, means for collecting magnetic particles and non-magnetic particles at the bottom of the chamber; multiple magnetic field producing means for producing, in the separation chamber, a magnetic field comprising a quadrupole magnetic field configuration superimposed on a dipole magnetic field configuration thereby defining a magnetic field gradient in the horizontal plane.

2. A magnetic separator according to claim 1 wherein the magnetic field producing means is quadrupole winding surrounded by a dipole winding.

3. A magnetic separator according to claim 2, wherein said quadrupole winding and said dipole winding both comprise superconductor windings.

4. A magnetic separator according to claim 1 wherein the separating chamber for the magnetic particles defines a dry route separator.

5. A magnetic separator according to claim 1 wherein the separating chamber for the magnetic particles defines a wet route separator.

* * * * *

UNITED STATES PATENT AND TRADEMARK OFFICE
CERTIFICATE OF CORRECTION

PATENT NO. : 4,608,155

DATED : August 26, 1986

INVENTOR(S) : Desportes et al.

It is certified that error appears in the above-identified patent and that said Letters Patent is hereby corrected as shown below:

Claim 1 at line 32 of Column 4, after "on a" insert --horizontal--.

Claim 2 at line 36 of Column 4, after "is" insert --a--.

Signed and Sealed this

Twenty-third Day of December, 1986

Attest:

DONALD J. QUIGG

Attesting Officer     Commissioner of Patents and Trademarks